United States Patent
Chi et al.

(10) Patent No.: US 11,759,520 B1
(45) Date of Patent: Sep. 19, 2023

(54) THERANOSTICS FOR PROTEIN MISFOLDING DISEASES

(71) Applicants: Eva Y. Chi, Albuquerque, NM (US); David G. Whitten, Albuquerque, NM (US); Patrick Donabedian, Albuquerque, NM (US); Florencia A. Monge, Albuquerque, NM (US); Matthew Creyer, Albuquerque, NM (US); Adeline Fanni, Albuquerque, NM (US); Jonathan Hulse, Albuquerque, NM (US)

(72) Inventors: Eva Y. Chi, Albuquerque, NM (US); David G. Whitten, Albuquerque, NM (US); Patrick Donabedian, Albuquerque, NM (US); Florencia A. Monge, Albuquerque, NM (US); Matthew Creyer, Albuquerque, NM (US); Adeline Fanni, Albuquerque, NM (US); Jonathan Hulse, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 0 days.

(21) Appl. No.: 16/285,809

(22) Filed: Feb. 26, 2019

Related U.S. Application Data

(60) Provisional application No. 62/635,360, filed on Feb. 26, 2018.

(51) Int. Cl.
*A61P 25/28* (2006.01)
*A61B 5/00* (2006.01)
*A61K 41/00* (2020.01)
*A61K 31/194* (2006.01)
*A61K 31/205* (2006.01)
*A61P 25/16* (2006.01)

(52) U.S. Cl.
CPC ........ *A61K 41/0057* (2013.01); *A61K 31/194* (2013.01); *A61K 31/205* (2013.01); *A61P 25/16* (2018.01); *A61P 25/28* (2018.01)

(58) Field of Classification Search
None
See application file for complete search history.

(56) References Cited

PUBLICATIONS

Donabedian et al., Oligo(p-phenylene ethynylene) Electrolytes: A Novel Molecular Scaffold for Optical Tracking of Amyloids ACS Chem. Neurosci. 2015, 6, 9, 1526-1535, Publication Date:Jun. 26, 2015 (Year: 2015).*
Pham et al., Crossing the blood-brain barrier: A potential application of myristoylated polyarginine for in vivo neuroimaging. NeuroImage vol. 28, Issue 1, Oct. 15, 2005, pp. 287-292 (Year: 2005).*
Donabedian, Patrick. Applied Photoproperties of Phenylene Ethynylenes, The university of New Mexico. Thesis 2016 https://digitalrepository.unm.edu/nsms_etds/33 (Year: 2016).*

\* cited by examiner

*Primary Examiner* — Aurora M Fontainhas
(74) *Attorney, Agent, or Firm* — Gonzales Patent Services; Ellen M. Gonzales

(57) ABSTRACT

Novel agents and theranostics for use as controllable and selective photosensitizers for the diagnosis, treatment and/or tracking of amyloid protein aggregates and amyloid diseases.

7 Claims, 14 Drawing Sheets

Aβ40 in Tris pH 8.0

Aβ40 in Tris pH 8.0
OPE1-

Aβ40 in Tris pH 8.0
OPE2+

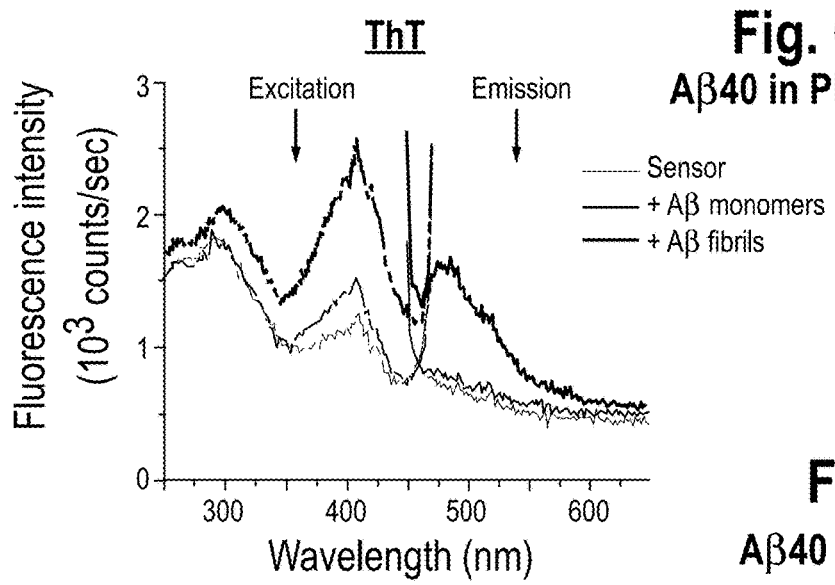
Fig. 6D Aβ40 in PB pH 7.4
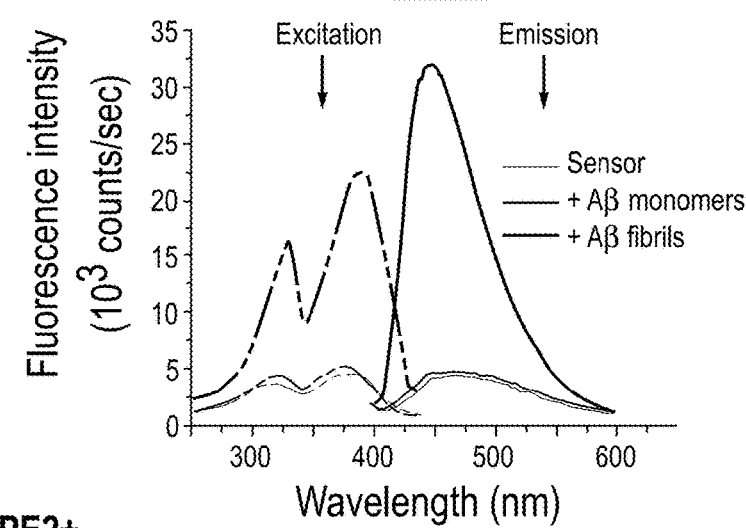
Fig. 6E Aβ40 in PB pH 7.4
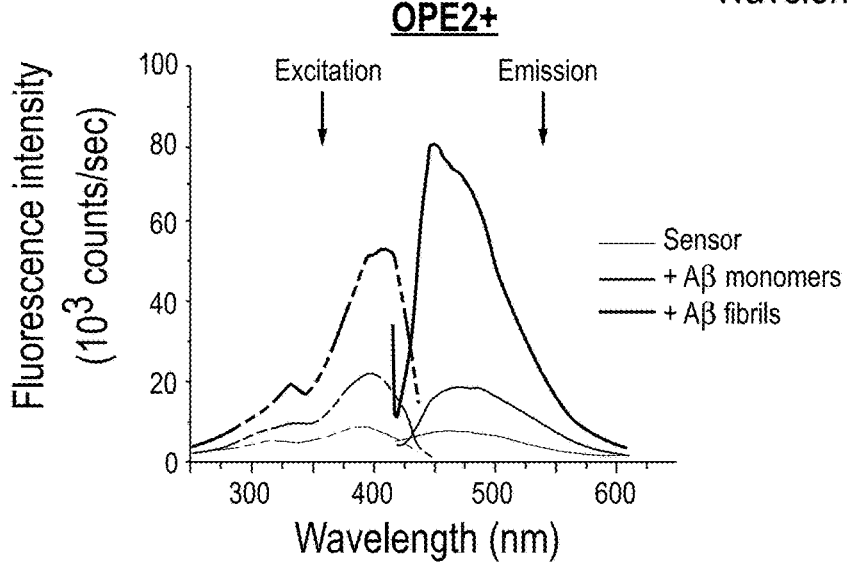
Fig. 6F Aβ40 in PB pH 7.4

WT ThT

WT OPE1-

WT OPE2+

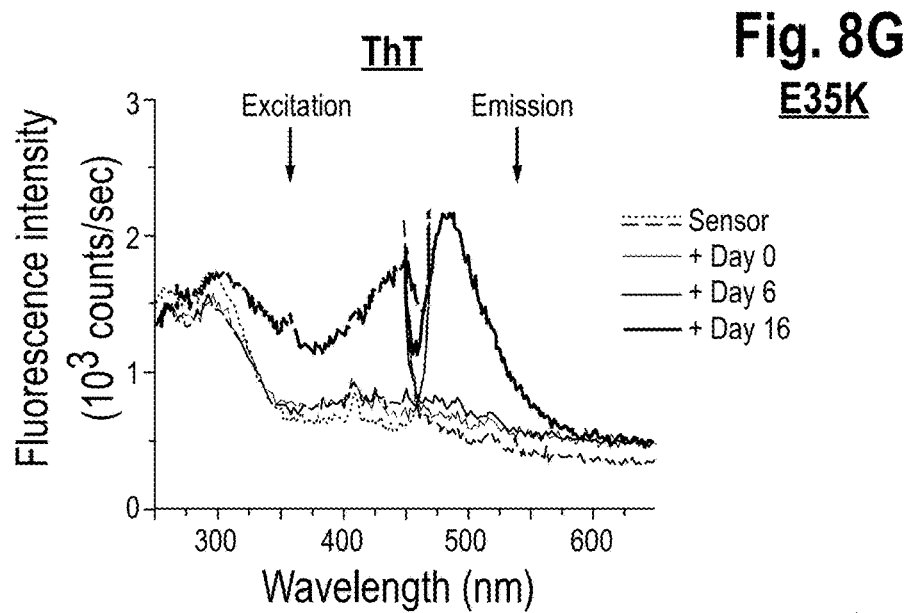
Fig. 8G E35K
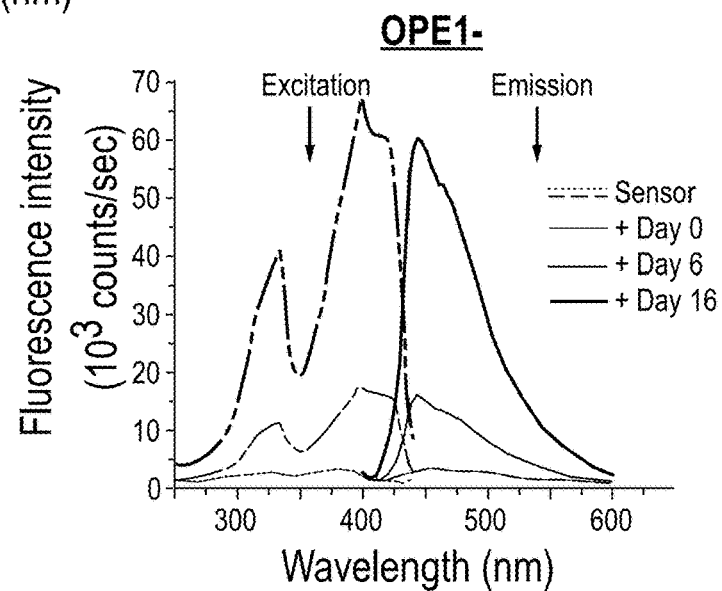
Fig. 8H E35K
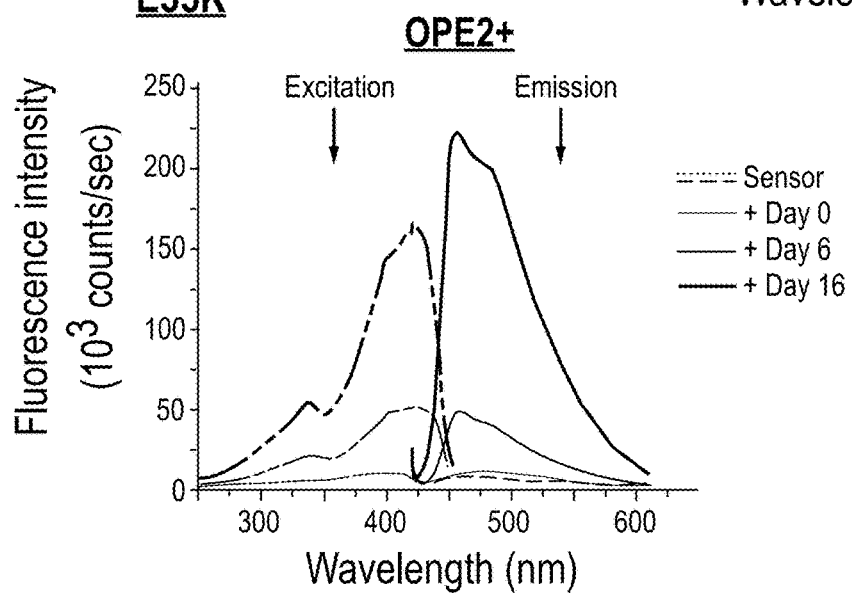
Fig. 8I E35K

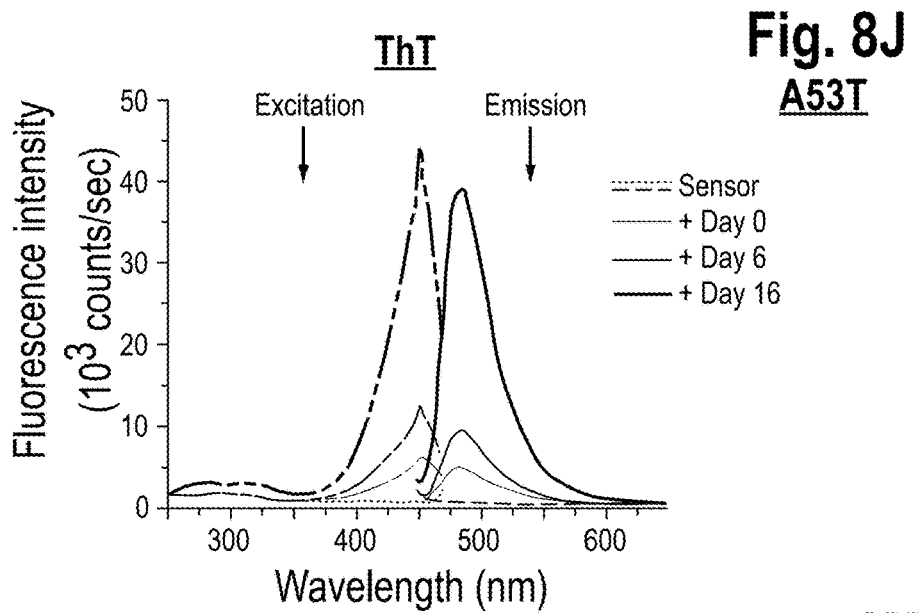
Fig. 8J A53T
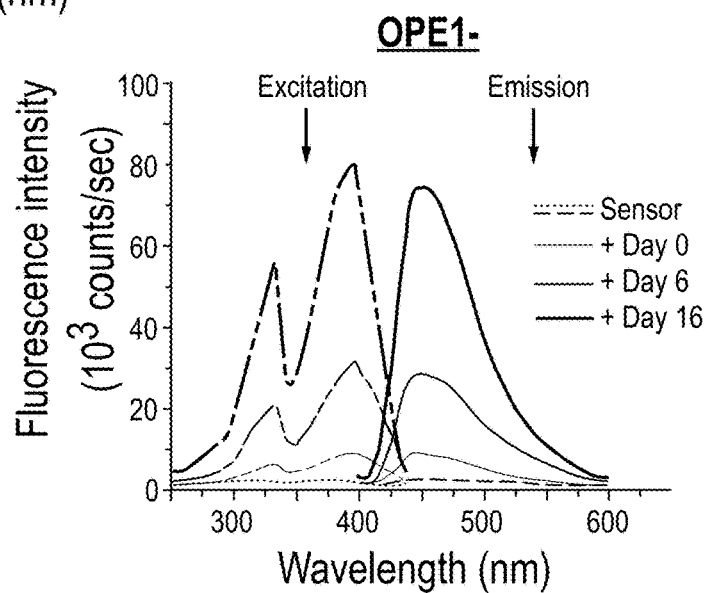
Fig. 8K A53T
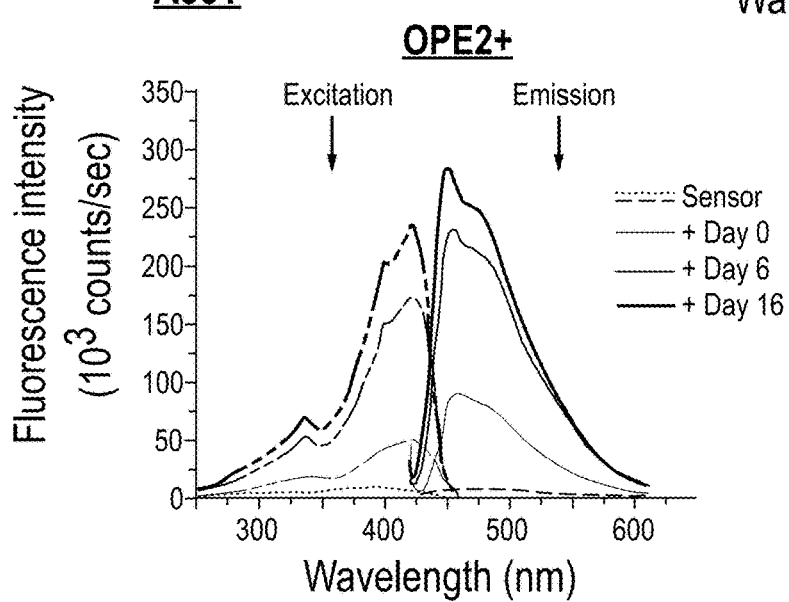
Fig. 8L A53T

Fig. 9A A: Dark
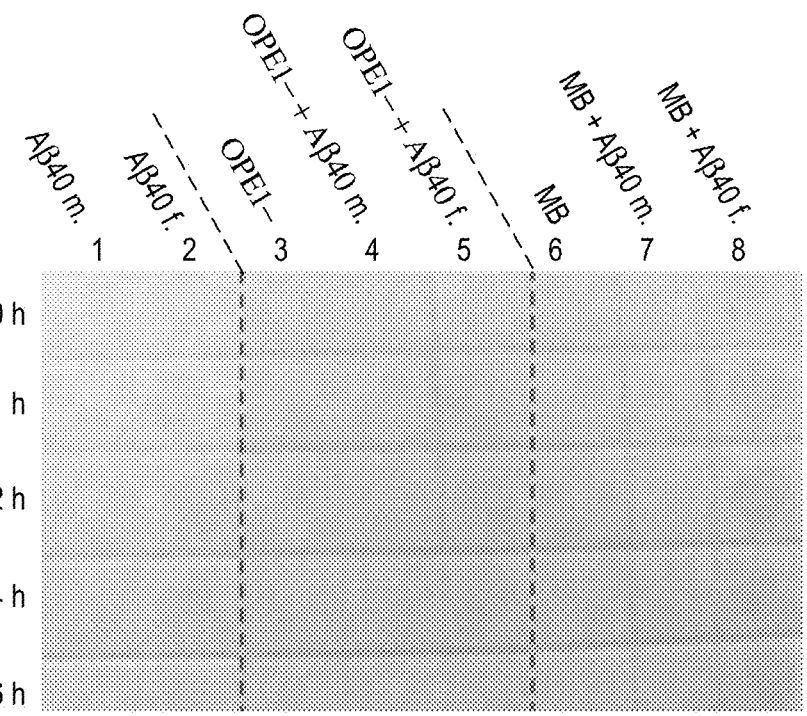
Fig. 9B B: Irradiated
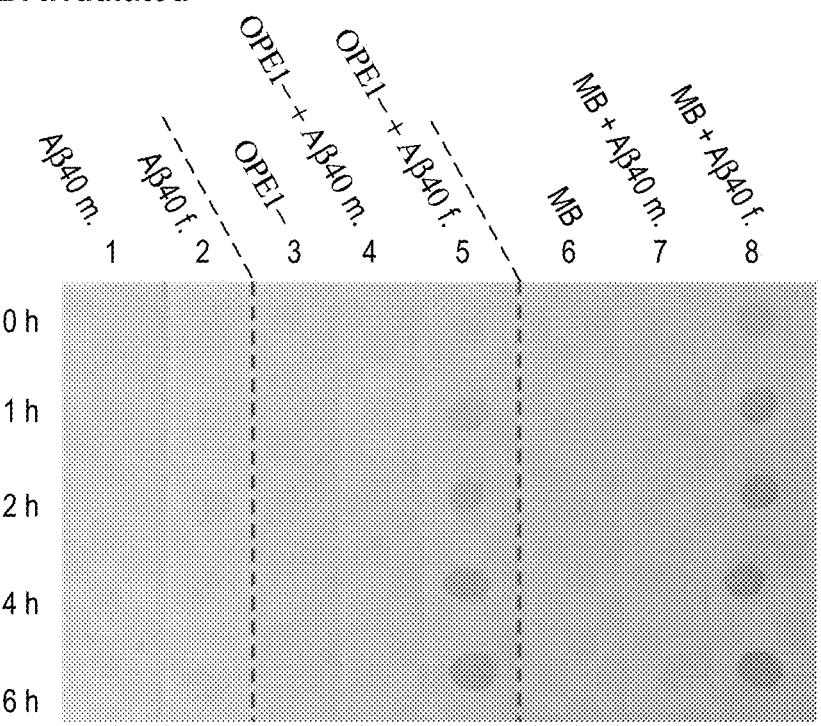

Fig. 13

$$\text{ADF} = \frac{F_{(dye + fibrils)} - F_{(dye + monomers)}}{F_{(dye\text{-}in\text{-}buffer)}}$$

THERANOSTICS FOR PROTEIN MISFOLDING DISEASES

CROSS-REFERENCE TO RELATED APPLICATIONS

The following application claims benefit of U.S. Provisional Application No. 62/635,360, filed Feb. 26, 2018, which is hereby incorporated by reference in its entirety.

STATEMENT REGARDING GOVERNMENT SPONSORED RESEARCH

This invention was made with Government support under Grant Nos. 1605225 and 1207362 awarded by the National Science Foundation (NSF and Grant No. HDTRA1-08-1-0053 awarded by the Defense Threat Reduction Agency. The U.S. Government has certain rights in this invention.

BACKGROUND

Theranostics is a growing field of medical research and treatment whereby treatment is determined and provided based on the detection of specific biological markers. In general, the aim is to use specific therapy agents to target specific biological targets such as, for example, specific receptors, or other aspects of biological pathways to provide a more targeted and hopefully more effective treatment option.

One avenue for theranostics involves the use of agents that generate reactive oxygen species as a product of photoexcited electronic states, i.e., so called "photosensitizers." The possibilities of spatially localized generation of reactive oxygen species (ROS) in response to irradiation are only just beginning to be explored, despite the more than 100-year history of phototherapy in modern medicine, and are already in the clinic in the form of photodynamic therapy (PDT) for cancers of the skin, esophagus and organ linings, actinic keratosis, and acne. (See e.g., Dolmans, et al., (2003) TIMELINE: Photodynamic therapy for cancer. *Nat. Rev. Cancer* 3, 380-387; Cui, et al., (2014) Reversible photoswitching of triplet-triplet annihilation upconversion using dithienylethene photochromic switches. *J. Am. Chem. Soc.* 136, 9256-9259; and Ericson, et al., (2008) Review of photodynamic therapy in actinic keratosis and basal cell carcinoma. *Ther. Clin. Risk Manag.* 4, 1-9.) Photodynamic destruction of pathogenic bacteria, viruses, and fungi is also under investigation for anti-biowarfare applications, passive sanitization of hospital surfaces under room light, and active sanitization of medical devices such as catheters. (See e.g., Johnson et al., (2013) Photoinactivation of gram positive and gram negative bacteria with the antimicrobial peptide (KLAKLAK)2 conjugated to the hydrophilic photosensitizer eosin y. *Bioconjug. Chem.* 24, 114-123; Li et al., (2014) Selective photodynamic inactivation of bacterial cells over mammalian cells by new triarylmethanes. *Langmuir* 30, 14573-80; Baptista et al., (2011) Photodynamic antimicrobial chemotherapy (PACT) for the treatment of malaria, leishmaniasis and trypanosomiasis. *Brazilian J. Med. Biol. Res.* 44, 1-10; Parthasarathy et al., (2015) Conjugated Polyelectrolytes with Imidazolium Solubilizing Groups. Properties and Application to Photodynamic Inactivation of Bacteria. *ACS Appl. Mater. Interfaces* 7, 28027-28034; and Pappas et al., (2016) Antifungal Properties of Cationic Phenylene Ethynylenes and Their Impact on β-Glucan Exposure. *Antimicrob. Agents Chemother.* 60, 4519-4529.) A major drawback of systemically dosed PDT photosensitizers, which are primarily porphyrins or their prodrugs, is their accumulation in the skin and eyes leading to long-lasting (weeks to months) post-therapeutic photosensitivity. (See, e.g., Allison et al., (2004) Photosensitizers in clinical PDT. *Photodiagnosis Photodyn. Ther.* 1, 27-42; and Moriwaki et al., (2001) Analysis of photosensitivity in Japanese cancer-bearing patients receiving photodynamic therapy with porfimer sodium (Photofrin). *Photodermatol. Photoimmunol. Photomed.* 17, 241-3.) Generation of ROS outside the target area can have multiple deleterious effects by overwhelming endogenous ROS-dependent signaling cascades. (See, e.g, Brieger et al., (2012) Reactive oxygen species: from health to disease. *Swiss Med. Wkly.* 142, w13659.) Accordingly, there is a need for photosensitizers that are both localized and controlled.

Previous investigations of switchable photosensitizers have used a pH-activatable rubyrin derivative, a quencher-tethered Si(IV) phthalocyanine and pyropheophorbide and various boron-dipyrromethene (BODIPY) dye-based scaffolds. (See, e.g., Tian et al., (2013) Cell-Specific and pH-Activatable Rubyrin-Loaded Nanoparticles for Highly Selective Near-Infrared Photodynamic Therapy against Cancer. *J. Am. Chem. Soc.* 135, 18850-18858; Lau et al., (2014) A dual activatable photosensitizer toward targeted photodynamic therapy. *J. Med. Chem.* 57, 4088-4097; Zheng et al., (2007) Photodynamic molecular beacon as an activatable photosensitizer based on protease-controlled singlet oxygen quenching and activation. *Proc. Natl. Acad. Sci.* 104, 8989-8994; Zhang et al., (2013) Photosensitizer that selectively generates singlet oxygen in nonpolar environments: Photophysical mechanism and efficiency for a covalent BODIPY dimer. *J. Phys. Chem. B* 117, 9050-9055; Kolemen et. al., (2015) Intracellular modulation of excited-state dynamics in a chromophore dyad: Differential enhancement of photocytotoxicity targeting cancer cells. *Angew. Chemie—Int. Ed.* 54, 5340-5344; and Jiang et al., (2015) Synthesis of NIR naphthyl-containing aza-BODIPYs and measure of the singlet oxygen generation. *Tetrahedron* 71, 7676-7680.) Solvent microenvironment has been used to selectively photooxidize proteins and cellular targets, but only using intramolecular FRET quenching or solvent polarity effects on photoelectron transfer in BODIPY monomers or covalently linked dimers. (See, e.g., Yogo, et al., (2008) Selective photoinactivation of protein function through environment-sensitive switching of singlet oxygen generation by photosensitizer. *Proc Natl Acad Sci USA* 105, 28-32 and Kolemen, et al., (2015) Intracellular modulation of excited-state dynamics in a chromophore dyad: Differential enhancement of photocytotoxicity targeting cancer cells. *Angew. Chemie—Int. Ed.* 54, 5340-5344.

Moreover, current therapeutic photosensitizers are primarily directed to cancer therapies. Accordingly, there is a need for controllable photosensitizers that target diseases and conditions other than cancer.

Amyloid protein misfolding and aggregation is associated with a wide range of diseases and conditions including, for example, Alzheimer's and Parkinson's diseases. While the mechanism is not entirely clear, it is believed that the toxic actions of amyloid aggregates such as amyloid-beta, tau, and alpha-synuclein proteins leads to the neurodegenerative impairment seen in diseases such as Alzheimer's and Parkinson's. Other diseases, conditions, or disorders that are associated with amyloid protein misfolding and aggregation include: Creutzfeldt Jakob, and Huntington's diseases, amyotrophic lateral sclerosis, rheumatoid arthritis, cardiac arrythmias, artherosclerosis, amyloidosis, and others.

Amyloid aggregates are formed after protein misfolding and self-association into small aggregates or oligomers that form larger structures called fibrils. Therapies for these diseases are limited and novel therapies are greatly desired. Accordingly, therapies that selectively degrade and cause the clearance of toxic amyloid aggregates, oligomers, and/or fibrils without interfering with the functional native proteins would be highly desirable.

Moreover, current methods for diagnosing many neurodegenerative diseases such as Alzheimer's are highly limited. Specifically, current diagnostic standards for Alzheimer's disease are based on neuropsychological evaluations. Unfortunately, patients displaying clinical symptoms may have already experienced extensive neuronal death in the decades that the disease progressed undetected. Earlier detection and diagnosis, particularly before any symptoms have been detected, could possible avoid substantial neuronal death and lead to much better outcomes.

SUMMARY

The present disclosure provides novel agents for use as controllable and selective photosensitizers (also referred to herein as a photosensitizing agents) that can lead to the oxidation of biomolecules. According to various embodiments, the agents can also be used as a theranostics for the diagnosis, treatment and/or tracking of amyloid disease including, but not limited to Alzheimer's and Parkinson's disease.

BRIEF DESCRIPTION OF THE DRAWINGS

FIG. 6D is the excitation and emission spectra of ThT in the presence of Aβ40 monomers or Aβ40 fibrils incubated in PB.

FIG. 6E is the excitation and emission spectra of OPE1− in the presence of Aβ40 monomers or Aβ40 fibrils incubated in PB.

FIG. 6F is the excitation and emission spectra of OPE2+ in the presence of Aβ40 monomers or Aβ40 fibrils incubated in PB.

FIG. 8G is the excitation and emission spectra of ThT in the presence of the E35K isoform of α-synuclein.

FIG. 8H is the excitation and emission spectra of OPE1− in the presence of the E35K isoform of α-synuclein.

FIG. 8I is the excitation and emission spectra of OPE2+ in the presence of the E35K isoform of α-synuclein.

FIG. 8J is the excitation and emission spectra of ThT in the presence of the A53T isoform of α-synuclein.

FIG. 8K is the excitation and emission spectra of OPE1− in the presence of the A53T isoform of α-synuclein.

FIG. 8L is the excitation and emission spectra of OPE2+ in the presence of the A53T isoform of α-synuclein.

FIG. 9A is a DNPH dot blot of Aβ40 monomers and fibrils in the presence of two photosensitizers OPE1$^{2-}$ and MB incubated in the dark between 0 and 6 hours.

FIG. 9B is a DNPH dot blot of Aβ40 monomers and fibrils in the presence of two photosensitizers OPE1$^{2-}$ and MB incubated under irradiation between 0 and 6 hours.

FIG. 13 is the formula that was used for determining the amyloid detector factor (ADF) described herein.

DETAILED DESCRIPTION

According to a first embodiment, the present disclosure provides a novel agent for use as a controllable and selective photosensitizer (also referred to herein as a photosensitizing agent) that can lead to the oxidation of biomolecules. For the purposes of the present disclosure, the term "controllable" in the context of a "controllable photosensitizing agent" is intended to mean that the photosensitizing activity is initiated only in response to one or more specific stimuli, such as binding of a specific target. Moreover, the term "selective" in the context of a "selective photosensitizing agent" is intended to mean that the agent preferentially causes photosensitization, of the desired target(s), such as amyloid protein aggregates (APAs), while leaving non-targets, such as the native protein(s), minimally disturbed or entirely undisturbed. For the purposes of the present disclosure, the term "amyloid protein aggregates" or "APAs" is intended to mean any amyloid-based product of protein misfolding or aggregate thereof including, but not necessarily limited to, aggregates, oligomers, and fibrils. For the purpose of the present disclosure, the term "minimally disturbed" is intended to mean that the non-targets remain largely unchanged physically and chemically.

According to a specific embodiment, the present disclosure provides a photosensitizing agent that is a localized photosensitizer with singlet oxygen-generating properties that can be controllably activated, for example, in response to binding to a specific target. The photosensitizing agent of the present disclosure may be a naturally occurring or synthetic oligomer, including, but not limited to those described in U.S. Pat. No. 10,092,000 "Structure, Synthesis, and Applications for Oligo Phenylene Ethynylenes (OPEs)" issued Oct. 9, 2018, U.S. Pat. No. 9,549,549 "Antimicrobial materials and methods" issued Jan. 24, 2017, U.S. Pat. No. 9,125,415 "Thiophene based oligomers as light activated biocides" issued Sep. 8, 2015, and U.S. Pat. No. 8,753,570 "Structure, synthesis, and applications for oligo phenylene ethynylenes" issued Jun. 17, 2014. According to a still more specific embodiment, the photosensitizing agent is or comprises an oligomeric p-phenylene ethynylene (OPE) or a derivative thereof. In general, OPEs contain a conjugated phenylene ethynylene backbone that is largely responsible for their sensing and photosensitizing activities and end and side groups that can be tailored for desired solubility, photophysical properties, and binding in applications such as biosensing and photosensitization. The size of these compounds can be precisely controlled by the number of phenylene ethynylene repeat units in the back bone. According to yet another more specific embodiment, the oxidizing agent is or comprises a bis(ethyl ester) phyenylene ethynylene (OPE1−), s-OPE$_2$(CO$_2$ET)$^{4+}$ (OPE2+), or a derivative thereof.

Figure 1:
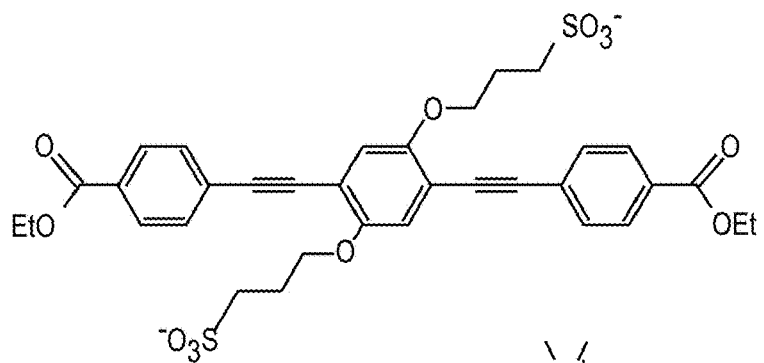
FIG. 1 is the chemical structure of OPE1−.

FIG. 1 provides the chemical structure of OPE1−. OPE1− is negatively charged and characterized by one repeat unit and two side chains each terminated with a sulfonate group. OPE1− selectively binds to detergents and APAs including, but not limited to, the amyloid-beta, tau, and alpha-synuclein proteins implicated in diseases such as Alzheimer's and Parkinson's. Moreover, binding of OPE1− to specific targets including APAs induces fluorescence leading to singlet oxygen generation. OPE1− may be synthesized or obtained using any suitable means including, but not limited to, the synthesis schemes described in Tang, et. al., (2011) "Synthesis, self-assembly, and photophysical properties of cationic oligo(p-phenyleneethynylenes)" *Langmuir* 27, 4945-55.

Figure 2:
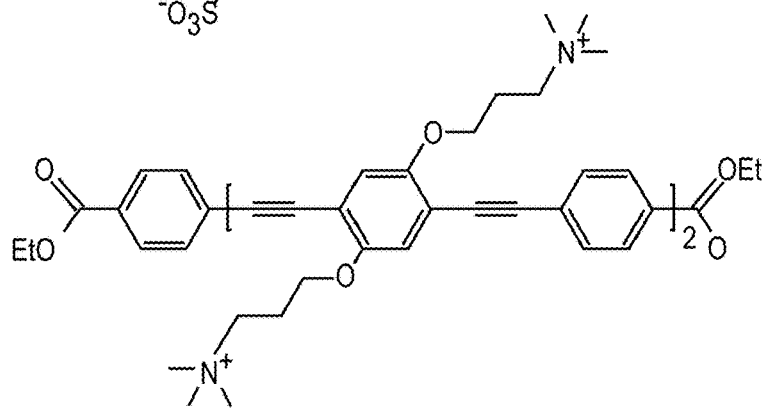
FIG. 2 is the chemical structure of OPE2+.

FIG. 2 provides the chemical structure of OPE2+. OPE2+ is a positively charged OPE characterized by two repeat units and two side chains each terminated with a quaternary amine group. Like OPE1−, OPE2+ selectively binds to aggregates of amyloid-beta, tau, and alpha-synuclein proteins and also like OPE1−, binding of OPE2+ induces OPE fluorescence leading to singlet oxygen generation. OPE2+ may be synthesized or obtained using any suitable means including, but not limited to, the procedures described in Tang, et al. (2010).

Figure 3:
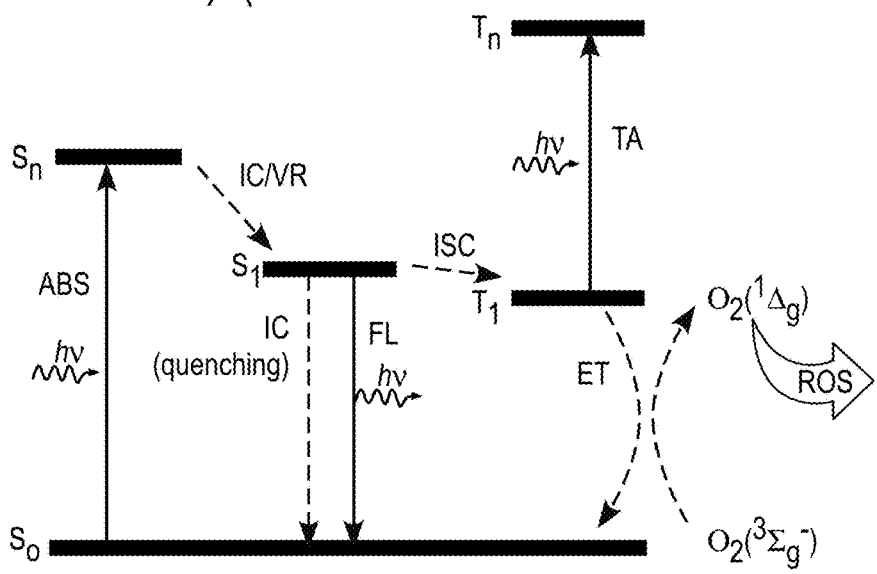
FIG. 3 is a simplified Jablonski diagram of OPE1− electronic states. After excitation by photon absorption (ABS) and fast internal conversion and vibrational relaxation (IC/VR) to the Si state, three competing decay processes exist: first, nonradiative, solvent-mediated quenching by internal conversion (IC), second, radiative decay by fluorescence (FL), and third, crossing to the triplet manifold by inter-system conversion (ISC) and subsequent energy transfer (ET) to produce singlet oxygen ($^1O_2$) from ground-state dioxygen. The relative rates of these three processes determine the functional behavior of the system. Triplet states can be assayed by the triplet-triplet transient absorption process (TA).

FIG. 3 depicts the control of photoexcited state populations in organic molecules by the presence of quenchers. In the system described herein, the quencher is the network of solvating interfacial water molecules at the end ester groups of OPEs and the tool for controlling the presence of the quencher is complexation of the dye with a binding partner, such as a surfactant, as described in Donabedian et al., (2017) "Detergent-induced self-assembly and controllable photosensitizer activity of diester phenylene ethynylenes" *PNAS* Vol. 114, No. 28, 7278-7282, or such as APAs, as described in the Experimental section below. The presence of ethyl ester substituents on a phenylene ethynylene backbone causes fluorescence to become highly quenched in water, presumably by quenching of the excited singlet state by an H-bonding or partial proton transfer mechanism. (See e.g., Tang et al., (2009) Photophysics and self-assembly of symmetrical and unsymmetrical cationic oligophenylene ethynylenes. *J. Photochem. Photobiol. A Chem.* 207, 4-6; Tang, et al., (2011) Synthesis, self-assembly, and photophysical properties of cationic oligo(p-phenyleneethynylene)s. *Langmuir* 27, 4945-55; and Hill et al., (2014) The influence of structured interfacial water on the photoluminescence of carboxyester-terminated oligo-p-phenylene ethynylenes. *J. Phys. Org. Chem.* 27, 252-257.)

Compared with previous efforts in the same field, the OPE-based system described herein is attractively compact, requiring no external quencher or specificity-granting conjugate. The quenching-granting groups add little steric bulk, and the compound's own binding profile provides the desired specificity.

It will be understood that it is important for the photosensitizing agent to specifically bind the disease-associated APAs while leaving the native protein undisturbed. As discussed in greater detail in the experimental section below, experiments studying the selective detection of OPE1− and OPE2+ of fibrillar and prefibrillar amyloid protein aggregates over the monomeric counterparts demonstrated a clear preference of the OPEs for the fibrillar and prefibrillar APAs. Moreover, comparisons between OPE1−/OPE2+ and thioflavin T (ThT), a well-known fibril dye, showed that the OPEs exhibited higher selectivity, higher binding affinity, and comparable limits of detection for Aβ40 fibrils compared to ThT. Moreover, the OPEs detected prefibrillar aggregates of Aβ42 and α-synuclein that ThT failed to detect.

Furthermore, as also discussed in the experimental section below, experiments studying the selective oxidation by OPE1− of A1340 fibrils over the monomeric counterpart demonstrated a clear preference of OPE1− for the A1340 fibrils. Comparisons between OPE1 and methylene blue (MB), a well-known sensitizer, demonstrated a striking difference in selectivity, with MB oxidizing both monomers and fibrils and OPE1− selectively oxidizing only the fibrils.

Figure 4:
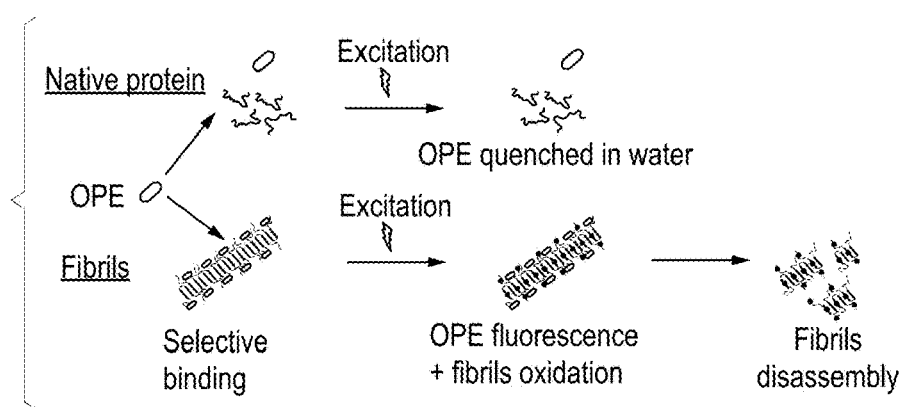
FIG. 4 is a schematic illustration of the use of an OPE as a photosensitizer for amyloid protein aggregates.

FIG. 4 is a schematic illustration of the mechanism by which an OPE acts as a selective photosensitizing agent which targets toxic APAs without affecting the native protein. As shown, the OPE is exposed to both native protein and APAs. The OPE selectively binds the APAs, but not the native protein. Photoexcitation of the unbound OPE has no effect, while photoexcitation of the bound OPE results in fluorescence and generation of singlet oxygen, which leads to oxidation and partial disassembly of the APAs. Under intra- or intercellular conditions, 99% of singlet oxygen cannot travel more than 300 nm from the site of its generation before it decays through the transfer of its electronic energy to vibrational modes of water; and the presence of redox sites will reduce this effective distance further. This less than 300 nm radius, being less than a cellular length, indicates that an active photosensitizer in or at a target cell will have minimal effect on adjacent cells.

According to a second embodiment, the present disclosure provides a novel agent for use in theranostic diagnosis and/or treatment of amyloid diseases. For the purposes of the present disclosure an "amyloid disease" is any disease, condition, or disorder that has been linked to or which is, or which is believed to be, associated with the presence of amyloids. Examples of amyloid diseases include, but are not limited to, Alzheimer's disease, diabetes mellitus type 2, Parkinson's disease, Transmissible spongiform encephalopathy, fatal familial insomnia, Huntington's disease, Medullary carcinoma of the thyroid, Cardiac arrhythmias, isolated atrial amyloidosis, atherosclerosis, rheumatoid arthritis, aortic medial amyloid, prolactinomas, familial amyloid polyneuropathy, hereditary non-neuropathic systemic amyloidosis, dialysis related amyloidosis, Finnish amyloidosis, Lattice corneal dystrophy, cerebral amyloid angiopathy, cerebral amyloid angiopathy (Icelandic type), systemic AL amyloidosis, and sporadic inclusion body myositis. According to a specific embodiment, the theranostic agent is a photosensitizing agent such as those described above.

As stated above, the present disclosure provides for a theranostic agent that may be used as a therapeutic agent for treatment or amelioration of diseases, conditions, or disorders associated with amyloid protein misfolding. In the case of use as a therapeutic, the theranostic may be administered by delivering a suitable therapeutic dosage of the novel theranostic to a patient under suitable conditions such that the theranostic agent can bind APAs present and then activating the theranostic agent in order to initiate oxidation of the APAs. According to a specific embodiment, the theranostic is an OPE, as described above, which may be delivered, for example, intravenously, to a patient.

According to some embodiments, the theranostic agent may be modified, as needed, to deliver the agent to a specific part of the patient's body. For example, the theranostic agent may be modified so as to enable or improve the ability or likelihood of the agent crossing the blood-brain barrier in order to reach APAs present in the brain (as would be desirable for diseases like Alzheimer's and Parkinson's). Suitable modifications may include, for example, the use of nanoparticles specifically designed for targeted drug delivery. Wohlfart et al., (2012). Transport of drugs across the blood-brain barrier by nanoparticles; *Journal of Controlled Release* 161(2), for example, describes the use of nanoparticles to transport drugs across the blood-brain barrier.

If the theranostic is a photosensitizer such as an OPE, local irradiation of the tissue of interest would then activate the photosensitizer to produce reactive oxygen species and damaging radicals that cause destruction to the APAs via direct oxidative damage of the tissue by the photosensitizer, and inflammatory cytokine mediated activation of the immune system (See, e.g., Dolmans et al., (2003) or another proteostasis (protein homeostasis) pathway. Suitable sources of irradiation include, but are not limited to, lasers and other lamp-based illumination sources. Other sources including the use of fiber optics and/or intratumoral LED arrays, which have been used for parenchymal organs like the liver and pancreas.

The theranostic may be administered alone, or in combination with other therapies.

As stated above, the present disclosure also provides a novel method for detecting the presence of APAs. In general, the method comprises delivering one or more of the theranostics described herein as a detectable APA-binding agent under suitable conditions that the APA-binding agent can bind to APAs and detect the presence of the binding agent. According to an embodiment, the APA-binding agent is an OPE as described above. The OPE may be modified to include a detectable label that is suitable for use with the specific detecting method being used. It will be understood that the detection method may be determined by the specific disease/condition/organ/system that is being evaluated. For example, in the case of Alzheimer's or Parkinson's diseases, it would be desirable to detect for the presence of APAs in the brain. In this case, a Positron Emission Tomography (PET) scan would be a suitable detection method and the OPE could be modified with a suitable radionuclide such as Fluorine-18. In this case, the OPE may also be modified to enable crossing of the blood-brain barrier, as described above, if needed. Of course it will be understood that PET scans can be used to interrogate other tissues and the OPEs could be modified to target other regions/tissues or could be allowed to travel throughout the body. Moreover, other detection modalities including, but not limited to, Diffuse Optical Imaging (DOI), Near-Infrared Spectroscopy (NIRS), and Event-related Optical Signal (EROS) could also be used.

According to still another embodiment, the theranostic of the present disclosure could be used to track disease progression by monitoring the presence or absence of APAs associated with a particular disease over time. Specifically, multiple doses of the theranostics of the present disclosure could be administered to a patient as described over a period of time. A care provider could then use this information to make determinations regarding the efficacy of current therapies, including whether or not to begin new treatments, care options, or the like.

Experimental

I. Selective Detection of Fibrillar and Prefibrillar Amyloid Protein Aggregates by OPE1− and OPE2+

Figure 5A:
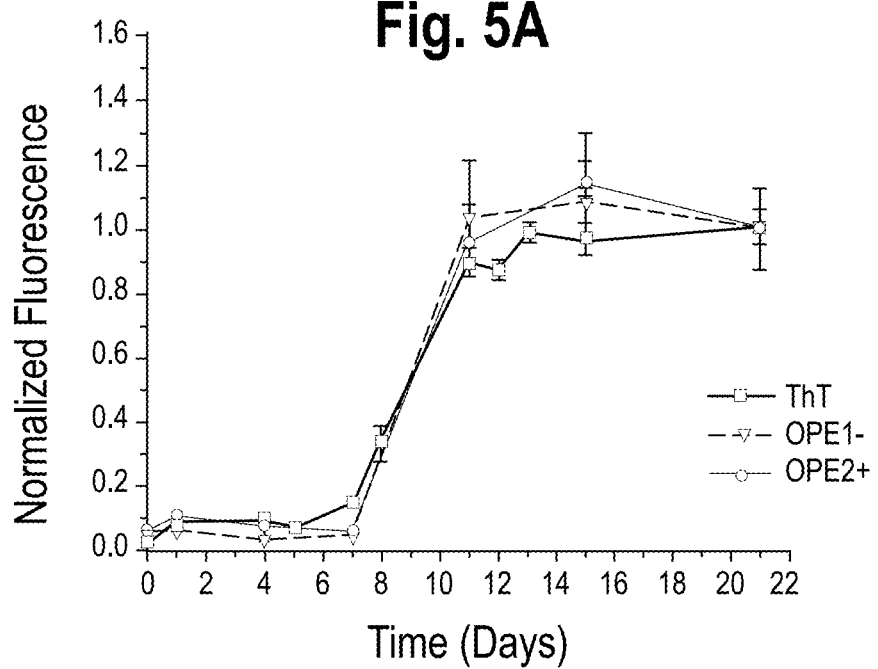
FIG. 5A is the fluorescence profile of ThT and OPE mixed with Aβ40 incubated in Tris pH 8.0 for various numbers of days.
Figure 5B:
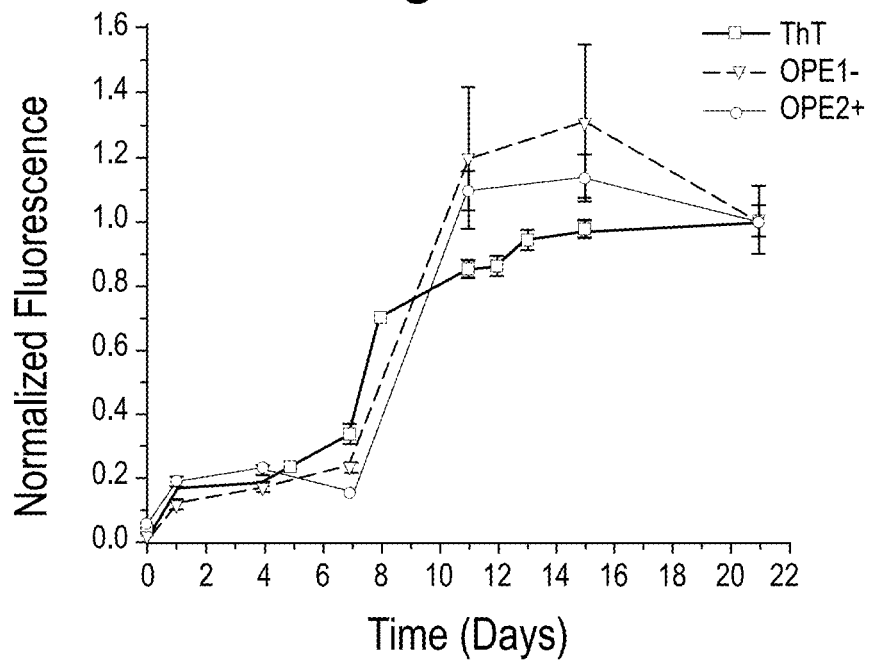
FIG. 5B is the fluorescence profile of ThT and OPE mixed with Aβ40 incubated in PB pH 7.4 for various numbers of days.
Figure 6A:
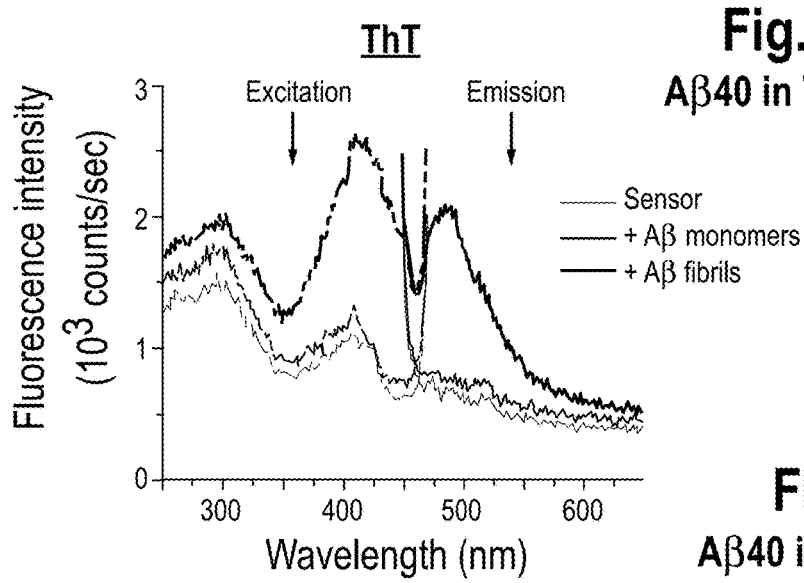
FIG. 6A is the excitation and emission spectra of ThT in the presence of Aβ40 monomers or Aβ40 fibrils incubated in Tris.
Figure 6B:
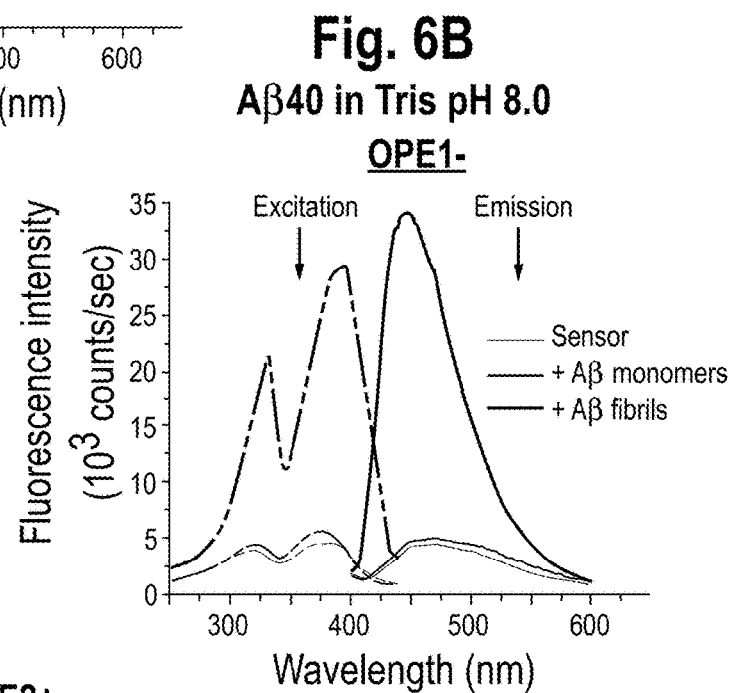
FIG. 6B is the excitation and emission spectra of OPE1− in the presence of Aβ40 monomers or Aβ40 fibrils incubated in Tris.
Figure 6C:
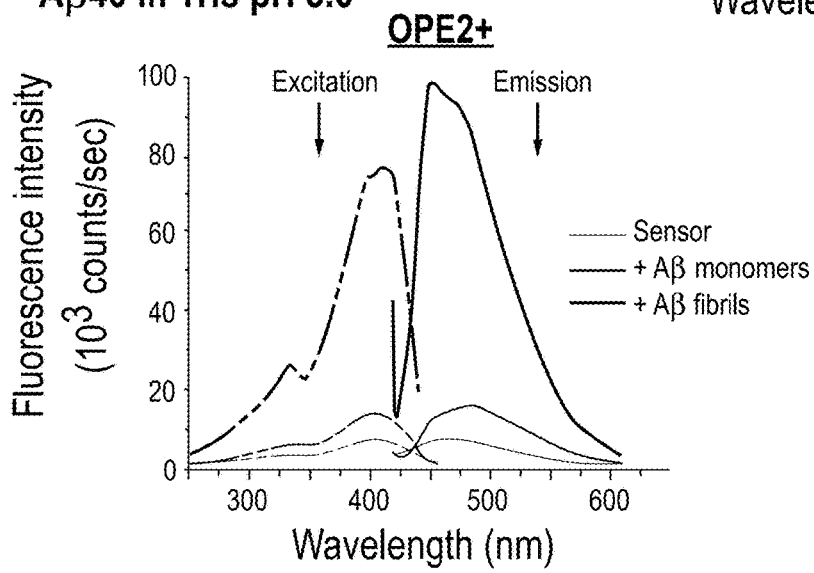
FIG. 6C is the excitation and emission spectra of OPE2+ in the presence of Aβ40 monomers or Aβ40 fibrils incubated in Tris.

FIGS. 5A and B show the fluorescence profiles of ThT (20 µM) and OPE (1 µM) mixed with Aβ40 fibrils (5 µM) incubated in Tris pH 8.0 (A) or PB pH 7.4 (B) for various numbers of days. It had previously been determined that using different incubation conditions (i.e. buffers) for Aβ40 resulted in fibrils having different physical characteristics, providing a good comparison for the variety of fibril formations that might be encountered in in vivo conditions. As shown in FIG. 5, normalized fluorescence intensities of the two OPEs yielded profiles similar to those obtained from ThT, indicating that the OPEs selectively detected the Aβ40 fibrils as well as ThT.

FIGS. 6A-6F provide the excitation and emission spectra of ThT, OPE, and OPE2+ alone and in the presence of Aβ40 monomers or Aβ40 fibrils incubated in the two different buffers. As expected, both OPEs showed low fluorescence intensities in the buffer alone. Importantly, no significant fluorescence increase was observed in the presence of Aβ40 monomers over the OPE background. While OPE2+ showed a small increase, it is believed this may be due to weak electrostatic interactions between the negatively charged peptide and the positively charged OPE. However, the small increase is noticeably less than the large fluorescent enhancement observed when the OPEs were mixed with Aβ40 fibrils. Moreover, the increase in fluorescence observed in the OPEs was significantly higher than the increase in fluorescence observed in ThT. Accordingly, our results show that the OPEs bind specifically and selectively to Aβ40 fibrils over Aβ40 monomers at a concentration significantly lower than the usually used ThT and induce 10 to 30-folds higher fluorescence intensity than ThT.

Quantitative assessment of OPE sensor performance towards A1340 fibrils at a 5 to 1 protein to sensor molar ratio was analyzed by calculating an amyloid detector factor using the equation shown in FIG. 13, where $F_{(dye-in-buffer)}$, $F_{(dye+fibrils)}$ and $F_{(dye+monomers)}$ are the integrated emission intensities for sensor alone, sensor in the presence of fibrils, and sensor in the presence of monomers, respectively. Using this equation, positive ADF values indicate selective sensing of fibrils over monomers, while negative ADF values indicate selective sensing of monomers. ADF values close to zero indicate no selective sensing. As shown in Table 1, all three sensors yield positive ADF values for Aβ40 sensing and both OPEs showed higher ADF values, or higher selectivity, than ThT. Moreover, analysis of the limits of detection and binding affinity (also shown in Table 1) showed that the OPEs displayed lower limits of detection and higher binding affinity than ThT.

content of the protein was monitored by DNPH dot blot, which increases as a result of histidine photooxidation.[20]

DNPH dot blot was carried out on Aβ40 fibrils and monomers incubated in the dark or under irradiation between 0 to 6 hours (FIGS. 9A and 9B). Aβ40 monomers and fibrils do not display any change in the carbonyl content after light exposure in the absence of photosensitizer (FIG. 9B, column 1 and 2). In the presence of both photosensitizers, OPE1- and MB, Aβ40 fibrils are characterized by an increase in the carbonyl content during irradiation (FIG. 9B, columns 5 and 8). Slightly higher carbonyl content in Aβ fibrils at time 0 h in the presence of MB could be due to short light exposure during sample preparation causing MB to photosensitize the oxidation of Aβ fibrils. When Aβ40 fibrils samples were incubated in the dark, no change was observed (FIG. 9A), indicating that both OPE1- and MB are light-controllable photo-oxidizers.

Figure 10A:
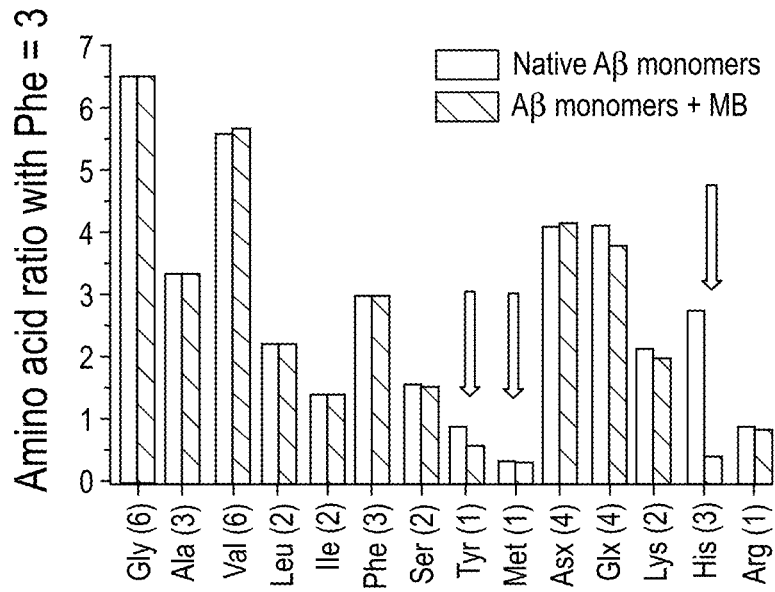
FIG. 10A is an amino acid analysis of Aβ40 monomers before and after 4 hour irradiation in the presence of methylene blue.
Figure 10B:
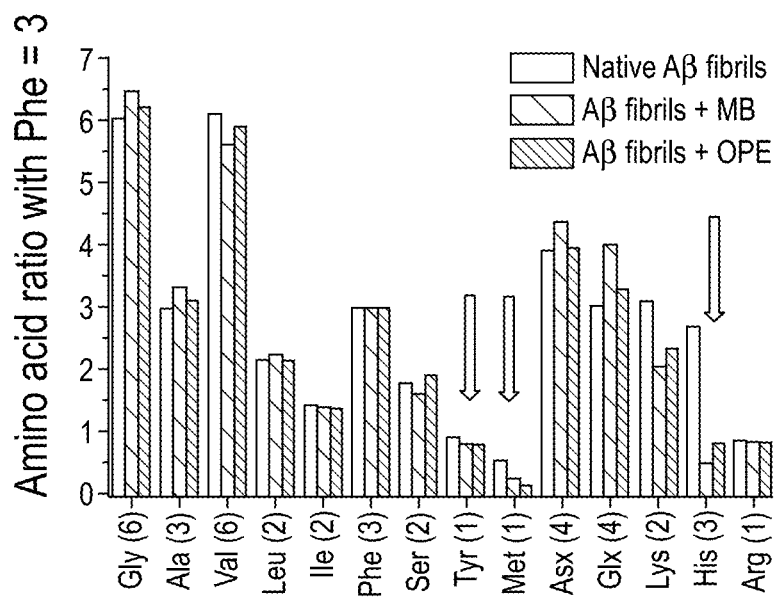
FIG. 10B is an amino acid analysis of Aβ40 monomers before and after 4 hour irradiation in the presence of methylene blue or OPE 1−.

To confirm this observation, Aβ40 monomers were analyzed by reverse phase HPLC (RP-HPLC), mass spectrometry (MS), and amino acid analysis (FIGS. 10A and B), before and after irradiation in the presence of OPE1- and MB. These additional characterizations showed that after irradiation in the presence of MB, Aβ40 monomers become more hydrophilic, present higher m/z ratio, and have a lower histidine content, which can be associated with peptide oxidation.

TABLE 1

Amyloid Detection Factor (ADF), Limit of Detection (LOD), and Dissociation Constan ($K_D$) for ThT, OPE 1-, and OPE 2+ Sensing of Aβ40 Fibrils produced in pH 8.0 Tris and in pH 7.4 PB

| | ADF | | LOD (μM) | | $K_D$ (μM) | |
|---|---|---|---|---|---|---|
| Sensor | Aβ40 in Tris | Aβ40 in PB | Aβ40 in Tris | Aβ40 in PB | Aβ40 in Tris | Aβ40 in PB |
| ThT | 0.53 +/- 0.1 | 0.23 +/- 0.03 | 0.65 +/- 0.05 | 0.69 +/- 0.05 | 2.7 +/- 1 | 5.1 +/- 2 |
| OPE1- | 2.8 +/- 0.6 | 2.3 +/- 0.3 | 0.52 +/- 0.04 | 0.48 +/- 0.02 | 0.70 +/- 0.1 | 0.27 +/- 0.04 |
| OPE2+ | 11 +/- 1 | 7.4 +/- 0.5 | 0.45 +/- 0.1 | 0.24 +/- 0.03 | 0.16 +/- 0.02 | 0.25 +/- 0.02 |

Figure 7A:
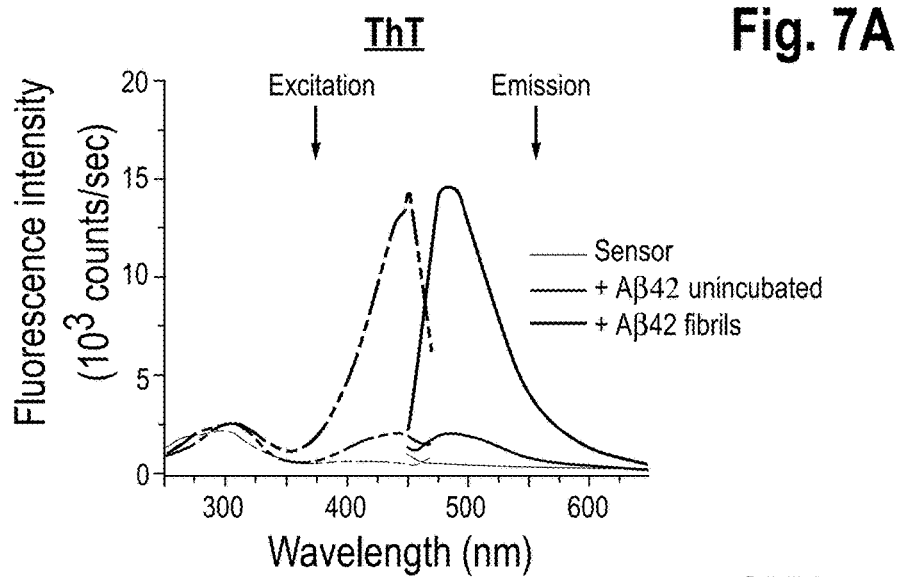
FIG. 7A is the excitation and emission spectra of ThT in the presence of Aβ42 monomers or Aβ42 fibrils.
Figure 7B:
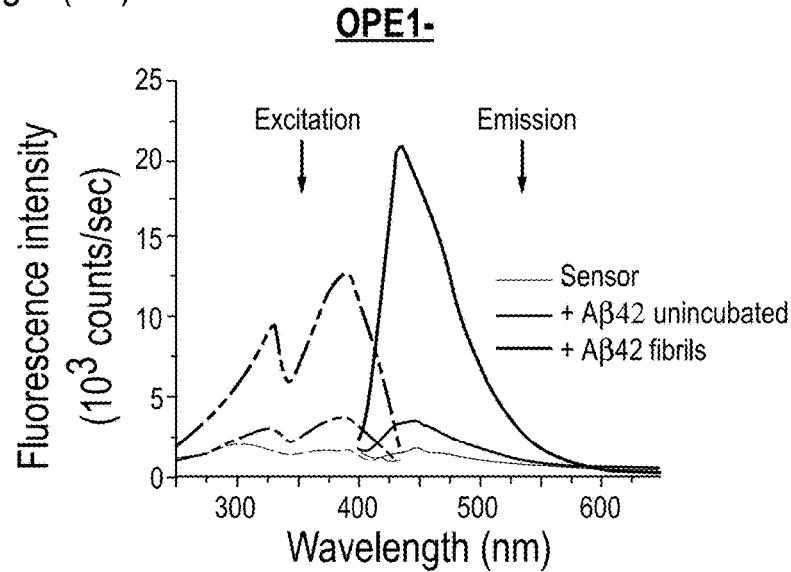
FIG. 7B is the excitation and emission spectra of OPE1− in the presence of Aβ42 monomers or Aβ42 fibrils.
Figure 7C:
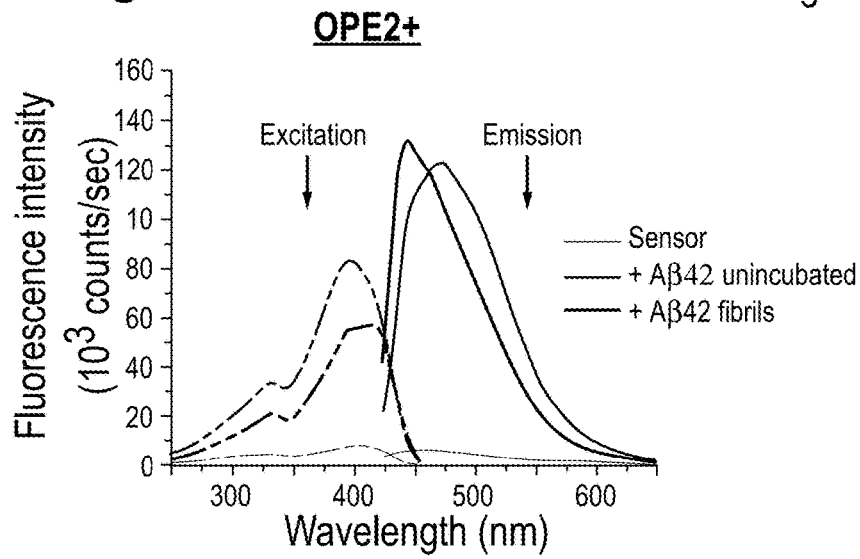
FIG. 7C is the excitation and emission spectra of OPE2+ in the presence of Aβ42 monomers or Aβ42 fibrils.
Figure 8A:
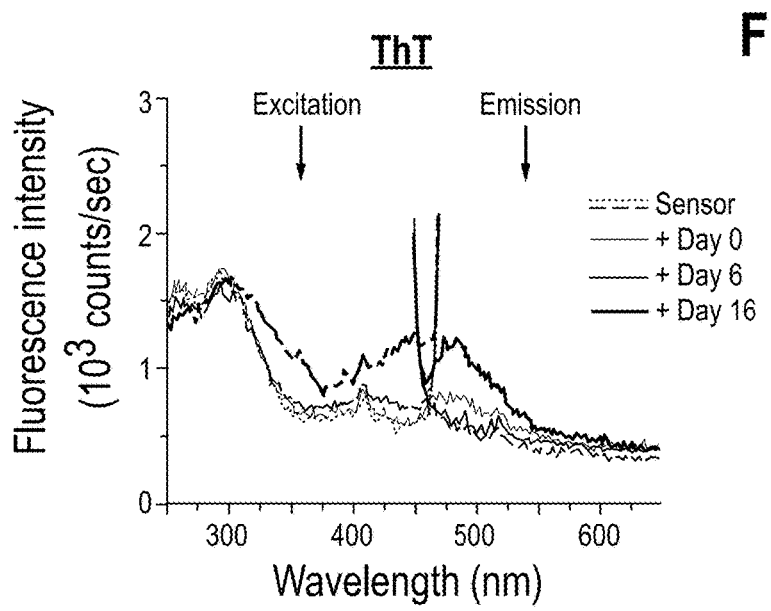
FIG. 8A is the excitation and emission spectra of ThT in the presence of the WT isoform of α-synuclein.
Figure 8B:
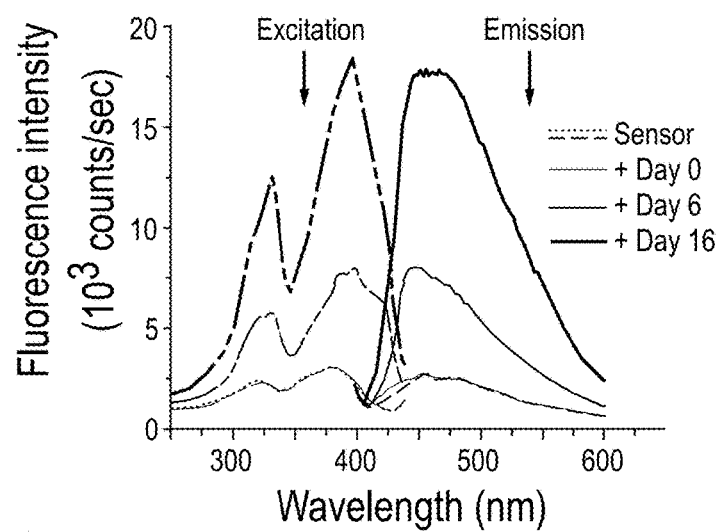
FIG. 8B is the excitation and emission spectra of OPE1− in the presence of the WT isoform of α-synuclein.
Figure 8C:
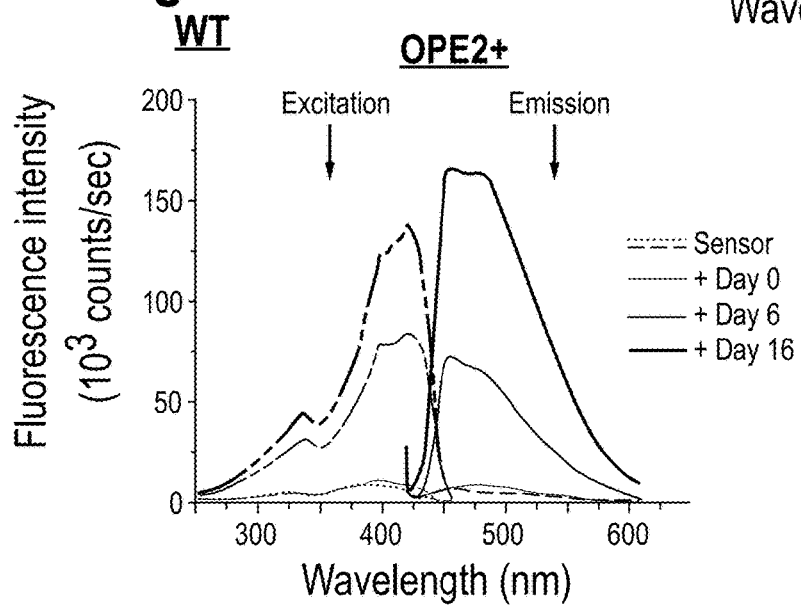
FIG. 8C is the excitation and emission spectra of OPE2+ in the presence of the WT isoform of α-synuclein.
Figure 8D:
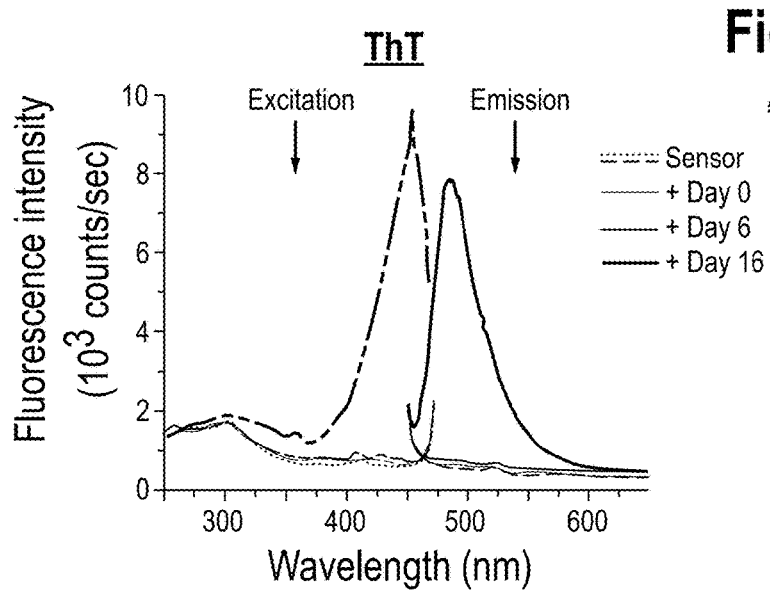
FIG. 8D is the excitation and emission spectra of ThT in the presence of the A30P isoform of α-synuclein.
Figure 8E:
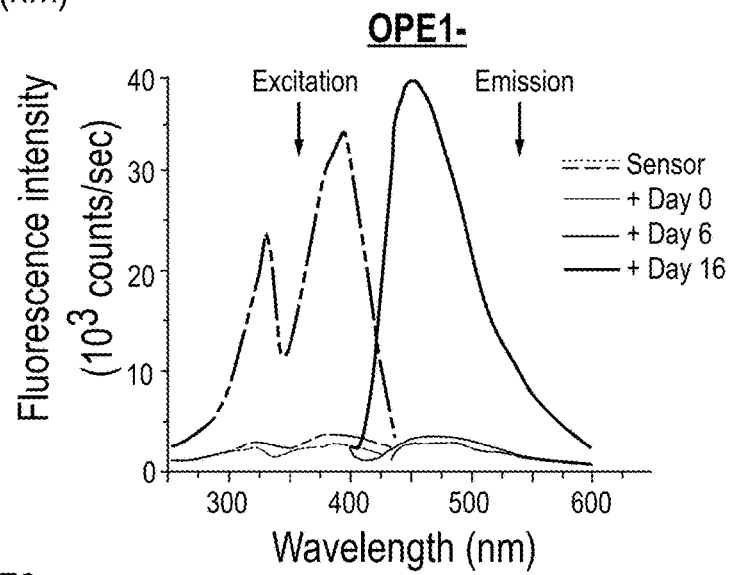
FIG. 8E is the excitation and emission spectra of OPE1− in the presence of the A30P isoform of α-synuclein.
Figure 8F:
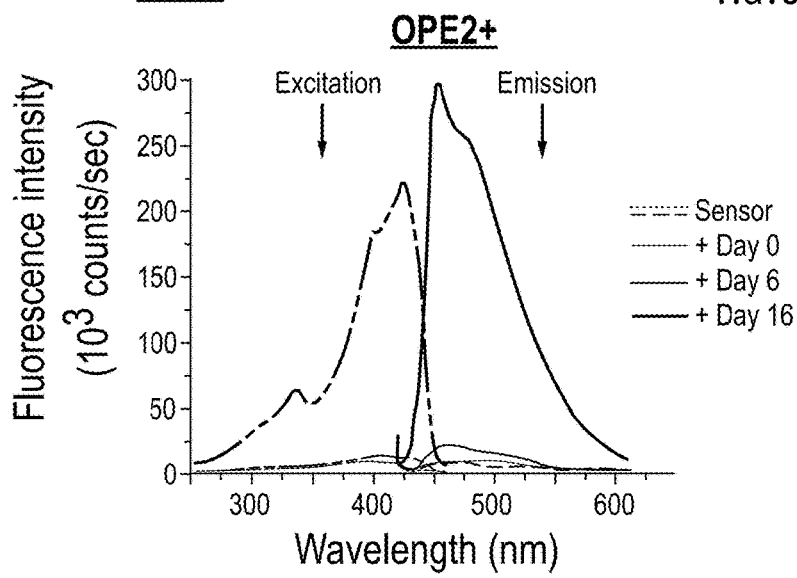
FIG. 8F is the excitation and emission spectra of OPE2+ in the presence of the A30P isoform of α-synuclein.

FIGS. 7A-7C show the fluorescence spectra of ThT (20 μM), OPE1- (1 μM) and OPE2 (1 μM) in the presence of unincubated (oligomeric) and incubated (fibrillar) Aβ42 peptide (5 μM). As shown, ThT and OPE1- exhibited small fluorescence increases with oligomeric Aβ42 and displayed large fluorescence increases in the presence of fibrils. Strikingly, OPE2+ showed large fluorescence enhancements with both prefibrillar and fibrillar aggregates of Aβ42.

FIGS. 8A-8L show the excitation and emission spectra of ThT, OPE1-, and OPE2+ alone and in the presence of four different isoforms of α-synuclein at 0, 6, and 16 days of incubation. Similar to the sensing of Aβ40 and Aβ42 fibrils, the OPEs exhibited larger fluorescence enhancement compared to ThT (2- to 20-fold higher for OPE1-, 6- to 100-fold higher for OPE2+). Moreover, the ADF values for ThT in the presence of the WT and E35K fibrils indicates poor fibril selectivity, while both OPES showed higher fibril selectivity of all α-synuclein proteins tested. Importantly, ThT was only able to detect A53T aggregates after 6 days of incubation (indicating ThT only detects fibrils) while both OPEs detected prefibrillar aggregates of the WT, E35K and A53T isoforms.

I. Selective Oxidation of Aβ40 Fibrils Over Aβ40 Monomers by OPE1

To evaluate the potency of OPE to selectively photo-oxidize Aβ40 fibrils over the monomeric counterpart, the oxidation state of both Aβ40 fibrils and monomers were characterized and were compared to MB. The carbonyl Taken together, DNPH dot blot, RP-HPLC and MS show that OPE1- selectively oxidized Aβ40 fibrils when exposed to light, while MB oxidized both Aβ40 monomers and fibrils when exposed to light.

III. Effect of Oxidation on Aβ40 Fibrils Disassembly

Figure 11A:
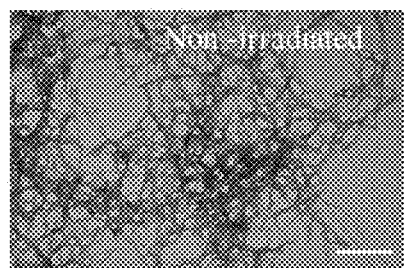
FIG. 11A is a TEM image of non-irradiated Aβ40 fibrils.
Figure 11B:
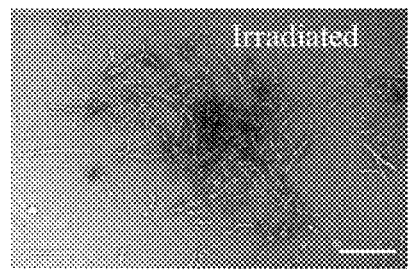
FIG. 11B is a TEM image of Aβ40 fibrils irradiated without exposure to a sensitizer.
Figure 11C:
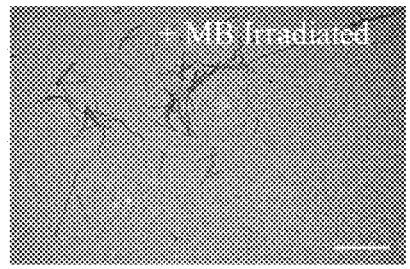
FIG. 11C is a TEM image of Aβ40 fibrils irradiated after exposure to methylene blue.
Figure 11D:
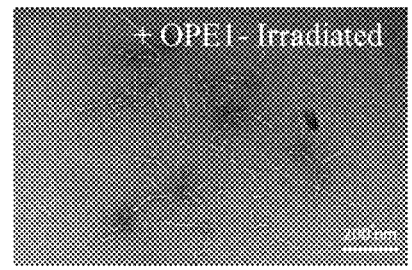
FIG. 11D is a TEM image of Aβ40 fibrils irradiated after exposure to OPE 1−.

The effect of fibril oxidation on their morphology and secondary structures was characterized by TEM imaging (FIGS. 11A-D) and circular dichroism (CD) spectroscopy (FIGS. 12A-C), respectively. As shown in FIG. 11A, native Aβ40 fibrils are long and form large matrices. After irradiation in the absence of photosensitizer, the fibrils matrices appear smaller but are still present (FIG. 11B). When the fibrils are irradiated with either MB (FIG. 11C) or OPE1- (FIG. 11D), fibrils dissociated and broke into shorter structures, which might be caused by oxidation of methionine located in the core of the fibrils, which could be involved in the stabilization of the long fibrils structure.

Figure 12A:
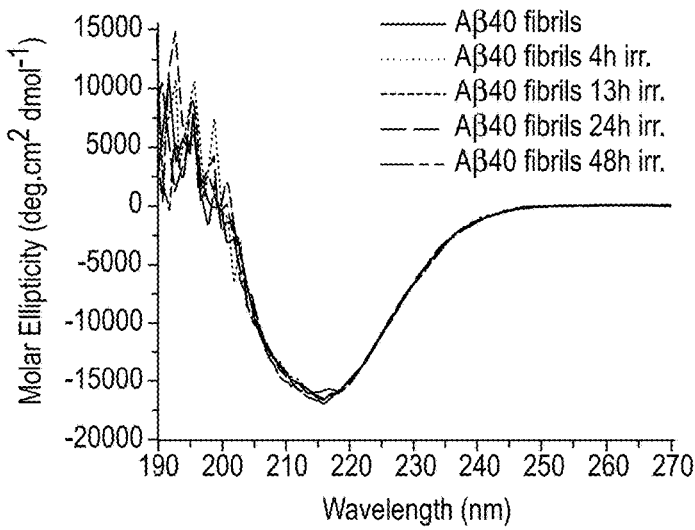
FIG. 12A is circular dichroism spectroscopy of Aβ40 fibrils irradiated without exposure to a sensitizer.
Figure 12B:
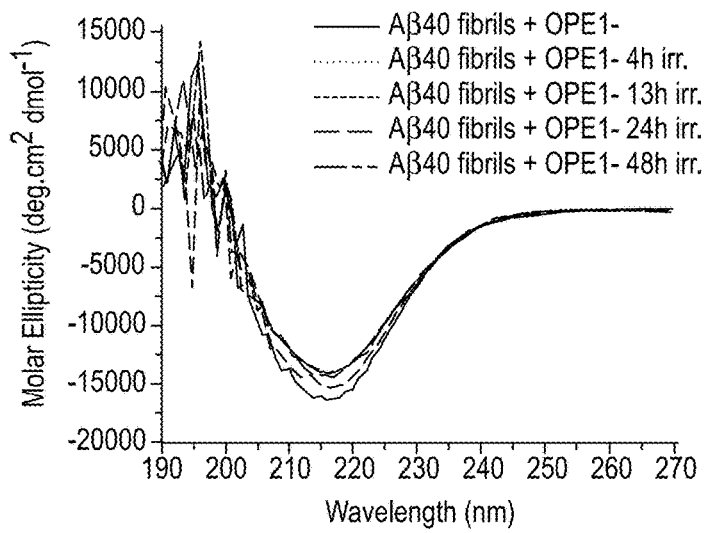
FIG. 12B is circular dichroism spectroscopy of Aβ40 fibrils irradiated after exposure to OPE 1−.
Figure 12C:
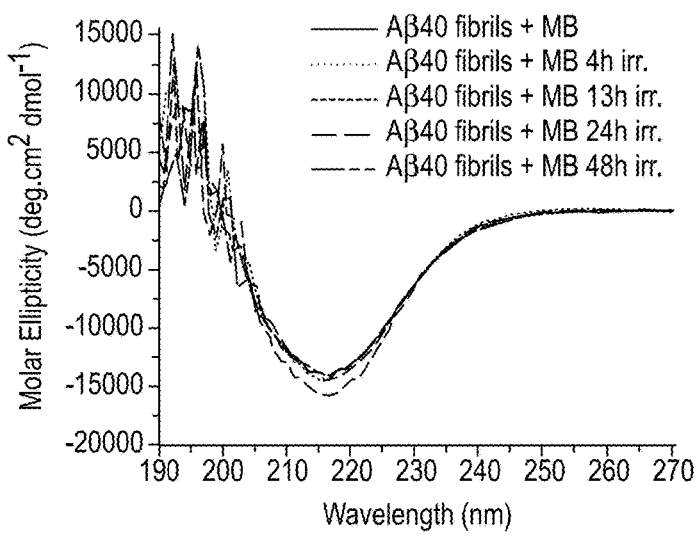
FIG. 12C is circular dichroism spectroscopy of A1340 fibrils irradiated after exposure to methylene blue.

The secondary structures of the fibrils were also analyzed (FIG. 12A-C). Aβ40 fibrils present a secondary structure rich in β-sheet with a peak at around 218 nm and was not affect by irradiation in the absence of sensitizer (FIG. 12A). After irradiation in the presence of OPE1- (FIG. 12B) or MB (FIG. 12C), no change in the secondary is observed, which support the hypothesis that as a result of oxidation, fibrils break down but still maintain their β-sheet structure.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. Furthermore, under no circumstances may the patent be interpreted to be limited to the specific examples or embodiments or methods specifically disclosed herein.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

What is claimed is:

1. A method for diagnosing and treating a patient with an amyloid-related disease, condition, or disorder comprising: delivering a theranostic agent comprising a detectable amyloid protein aggregate (APA)-specific agent capable of singlet oxygen generation under suitable conditions that the APA-specific agent can specifically bind to APAs associated with the amyloid-related disease, condition, or disorder without binding to the native protein; detecting the presence of the bound theranostic agent and irradiating a region of the patient believed to be associated with the disease so as to activate the bound APA specific agent and generate singlet oxygen resulting in selective oxidation of the bound APAs, wherein the theranostic agent comprises an oligomeric p-phenylene ethynylene (OPE).

2. The method of claim 1 wherein the OPE is OPE 1−.

3. The method of claim 1 wherein the OPE is OPE 2+.

4. The method of claim 1 comprising delivering the theranostic agent at least twice and comparing the presence of the bound theranostic agent after each delivery so as to produce an analysis of the progression of the amyloid-related disease, condition, or disorder.

5. The method of claim 1 wherein the theranostic agent is able to cross the blood-brain barrier.

6. The method of claim 1 wherein the amyloid-related disease is Parkinson's disease.

7. The method of claim 1 wherein the amyloid-related disease is Alzheimer's disease.

* * * * *